United States Patent [19]

Willcockson, deceased et al.

[11] Patent Number: 4,477,438
[45] Date of Patent: Oct. 16, 1984

[54] HYDROGEN PEROXIDE COMPOSITION

[75] Inventors: George W. Willcockson, deceased, late of Dallas, Tex., by Beth E. Willcockson, executrix; David C. F. Law, Arlington, Tex.

[73] Assignee: Surgikos, Inc., Arlington, Tex.

[21] Appl. No.: 441,006

[22] Filed: Nov. 12, 1982

[51] Int. Cl.³ .................. A01N 59/00; A61K 33/40
[52] U.S. Cl. ................................ 424/130; 252/390
[58] Field of Search ............... 424/130; 423/272, 273

[56] References Cited

U.S. PATENT DOCUMENTS

| | | | |
|---|---|---|---|
| 2,680,674 | 6/1954 | Cooper et al. | 423/273 |
| 3,053,634 | 9/1962 | Luten et al. | 423/272 |
| 4,051,058 | 9/1977 | Gross Böwing et al. | 424/130 |
| 4,103,001 | 7/1978 | Schattner | 424/148 |
| 4,214,050 | 7/1980 | Blay | 424/130 X |

Primary Examiner—Leonard Schenkman
Attorney, Agent, or Firm—Michael Q. Tatlow

[57] ABSTRACT

An antimicrobial composition containing hydrogen peroxide is disclosed. The composition is non-corrosive to surgical instruments and contains 4%–7% hydrogen peroxide, 0.1% to 0.3% of a chelating agent, 0.1% of a water soluble zinc compound, 0.1% to 0.3% of a sodium cocoyl sarcosinate or is fatty acid-based analogs, an anionic surfactant selected from the group consisting of sodium n-decyl diphenylether disulfonate or sodium lauryl sulfate and a buffer system to maintain the pH of the composition in a pH range of from 4 to 6.

4 Claims, No Drawings

HYDROGEN PEROXIDE COMPOSITION

FIELD OF THE INVENTION

This invention relates to an improved hydrogen-peroxide-based sterilizing and disinfecting solution which is stabilized to prevent decomposition of hydrogen peroxide and to prevent corrosion damage to medical instruments contacted with the solution.

BACKGROUND OF THE INVENTION

It has long been recognized that hydrogen peroxide can be employed as an antimicrobial agent to sterilize and disinfect environmental surfaces and surgical instruments. However, hydrogen peroxide has not been extensively used as an antimicrobial agent for hospital equipment because of its instability and because it tends to corrode surgical instruments. Aqueous solutions of hydrogen peroxide are inherently corrosive to a variety of metals such as iron, nickel, copper, chrome and their alloys. Corrosion of these metals when in contact with a hydrogen peroxide solution produces ions which catalyze the decomposition of hydrogen peroxide and accelerate the loss of the antimicrobial activity of the solution. The decomposition of hydrogen peroxide is accompanied by the release of the oxygen which, if allowed to accumulate in a closed container, can create a fire or explosion hazard.

There have been numerous attempts to stabilize hydrogen peroxide to prevent its rapid decomposition.

U.S. Pat. No. 3,053,634 discloses a composition containing hydrogen peroxide, a chelating agent, an aluminum compound and a phosphate salt.

U.S. Pat. No. 2,961,306 discloses a composition containing 50%/80% hydrogen peroxide and 0.001%–1% 1,2-diaminocyclohexane tetraacetic acid.

U.S. Pat. No. 3,089,753 and 3,208,825 disclose compositions having pH values of about 3.3 and 2.5, respectively, containing hydrogen peroxide, a chelating agent, a thin compound such as $Na_2SnO_3$ and a phosphate salt.

U.S. Pat. No. 2,680,674 discloses a composition containing hydrogen peroxide and a zinc or cadmium compound such as the sulfate, nitrate or chloride.

Kassem et al. disclose the use of ethylenediamine tetraacetic acid to stabilize hydrogen peroxide against the catalytic effects of iron and zinc. See *Chemical Abstracts* 78:164666H and 78:164667J.

We have found that the stabilizer systems mentioned in the above-cited references are insufficient to prevent the corrosion of surgical instruments or the decomposition of hydrogen peroxide when the hydrogen peroxide solution is used as a sterilizing and disinfecting agent.

SUMMARY OF THE INVENTION

The present invention provides a sterilizing and disinfecting solution in which hydrogen peroxide is the active ingredient and in which the solution is stabilized against the decomposition of the hydrogen peroxide and which solution will not excessively corrode surgical instruments. The solution has excellent sterilization and disinfecting properties and can be used to sterilize sophisticated medical instruments such as endoscopes without causing excessive damage to such instruments. The present composition contains a number of ingredients each of which is necessary in the composition to produce the desired result. These ingredients are the following:

1. Hydrogen Peroxide.
2. A nitrogen-containing chelating agent such as N-(hydroxyethyl)ethylenediamine-triacetic acid (HEEDTA), ethylenediamine-tetraacetic acid (EDTA), or diethylenetriamine-pentaacetic acid (DTPA) or their sodium salts.
3. A water soluble zinc compound such a zinc sulfate, zinc acetate, zinc nitrate or zinc gluconate.
4. A sarcosinate surfactant such as sodium cocoyl sarcosinate or sodium lauryl sarcosinate.
5. An anionic surfactant selected from the group consisting of sodium n-decyl diphenylether disulfonate or sodium lauryl sulfate.
6. A buffer composition such as sodium acetate, sodium phosphate, sodium borate or mixtures thereof to maintain the pH of the aqueous solution at a level of from pH 4.5 to pH 5.5.

DETAILED DESCRIPTION OF THE INVENTION

The compositions of this invention are aqueous solutions containing the following ingredients: (all percentages are by weight based on the total weight of the solution)

(1) Hydrogen peroxide ($H_2O_2$), in a concentration between 4% and 7%.

(2) A nitrogen-containing chelating agent such as N-(hydroxyethyl)-ethylenediaminetriacetic acid (HEEDTA), ethylenediaminetetraacetic acid (EDTA), and diethylenetriaminepentaacetic acid (DTPA) or their sodium salts, in a concentration from 0.1% to 0.39%.

(3) A soluble compound containing zinc ions such as zinc sulfate, zinc acetate, zinc nitrate or zinc gluconate in a concentration of about 0.1%. The presence of the zinc in the formulation provides improved corrosion inhibition against copper and nickel and maintains the transparency of the solution. The preferred zinc compound is zinc sulfate heptahydrate.

(4) Sodium cocoyl sarcosinate and its fatty acid-based analogs of the structure:

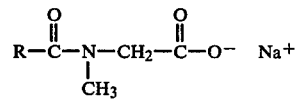

where R is a hydrocarbon chain having between 11 and 14 carbon atoms. These are employed at a concentration of 0.1% to 0.3%.

(5) An anionic surfactant selected from the group consisting of sodium n-decyl diphenylether disulfonate and sodium lauryl sulfate in a concentration from 0.1% to 0.3%.

(6) A buffer operating in the pH range from 4 to 6, such as sodium acetate, sodium phosphate and sodium borate. The buffer concentration range may be 0.5% or below.

It has been found that all of the above-mentioned ingredients are necessary in order to obtain a satisfactory solution with the desired stability, non-corrosiveness and antimicrobial properties.

A composition containing the above-mentioned ingredients provides excellent antimicrobial activity and does not excessively corrode surgical instruments. The composition can be used at room temperatures and at elevated temperatures, e.g., 40° C. to 50° C. The antimicrobial activity of the composition is enhanced if the composition is employed at an elevated temperature. At elevated temperatures, the composition will disinfect and sterilize in a shorter time period than at room temperature. However, the composition is an effective disinfecting solution at room temperatures in reasonable time periods.

In addition to the ingredients specified above, the composition of the present invention may also contain optimal inactive ingredients such as a dye, for example FD&C Yellow #5. The present composition may be packaged as a single component with all the ingredients in one container or may be packaged as a two-component system. As a two-component system, the hydrogen peroxide is mixed with water and placed in one container. The remaining ingredients are placed in a second container with a small amount of water, and the contents of the two containers are thoroughly mixed immediately prior to use. When the two-component system is used, a small amount of a surfactant, which is a condensate of ethylene oxide with propylene glycol and propylene oxide, e.g., PLURONIC P104 (BASF Wyandotte), may be added to the second container to maintain homogenicity of the ingredients.

The sporicidal test employed in the following Examples is the A.O.A.C. Sporicidal Test as specified in *Official Methods of Analysis* of the Association of Official Analytical Chemists (A.O.A.C.) 13th Edition, 1980 Sections 4.015–4.017. The Use Dilution Test is employed in Sections 4.007–4.011; The Fungicidal Test is employed in Sections 4.018–4.022, and the Tuberculocidal Test is employed in Sections 4.048–4.050 of the same publication.

In the Examples, all percentages are weight percent unless otherwise indicated.

EXAMPLE I

This Example shows that the compositions of the present invention have excellent antimicrobial properties, and the compositions do not cause corrosion of surgical instruments.

Two solutions containing 6% hydrogen peroxide were prepared according to the formulations set forth in Table 1A.

TABLE 1A

Compositions of Sterilizing/Disinfecting Solutions

| Ingredients | Formulation I (Weight Percent) | Formulation II (Weight Percent) |
|---|---|---|
| Hydrogen peroxide | 6.0 | 6.0 |
| Acetic Acid | ca. 0.1 | ca. 0.1 |
| Zinc sulfate (7H$_2$O) | 0.1 | 0.1 |
| HEEDTA* | 0.3 | 0.3 |
| Sodium cocoyl sarcosinate | 0.3 | 0.3 |
| Sodium lauryl sulfate | 0.15 | — |
| Sodium n-decyl diphenylether disulfonate | — | 0.15 |
| Water | remainder | remainder |
| Solution pH | 5.0 | 5.0 |

*N—(hydroxyethyl)ethylenediamine triacetic acid

The formulations were tested against various organisms at a temperature of 40° C., and the results are shown in Table 1B.

TABLE 1B

| Organisms | Carriers | Exposure Time (minutes) | Rates in AOAC Sporicidal or Use Dilution Tests Form. I | Form. II |
|---|---|---|---|---|
| Sporicidal Test | | | | |
| B. subtilis spores | porcelain | 30 | 0/60 | 0/60 |
| | | 45 | 0/60 | 0/60 |
| | | 60 | 0/60 | 0/60 |
| | silk suture | 30 | 1/60 | 0/60 |
| | | 45 | 1/60 | 0/60 |
| | | 60 | 0/60 | 0/60 |
| C. sporogenes spores | porcelain | 30 | 2/60 | 2/60 |
| | | 45 | 1/60 | 0/60 |
| | | 60 | 0/60 | 0/60 |
| | silk suture | 30 | 0/60 | 0/60 |
| | | 45 | 0/60 | 0/60 |
| | | 60 | 0/60 | 0/60 |
| Use Dilution Test | | | | |
| S. aureus | stainless steel | 10 | 1/60 | 0/60 |
| P. aeruginosa | stainless steel | 10 | 0/60 | 0/60 |
| S. choleraesuis | stainless steel | 10 | 0/60 | 0/60 |

In an AOAC Sporicidal Test, one failure in 60 is not acceptable.

The Environmental Protection Agency considers a failure rate of 1/60 in a Use Dilution Test as above the minimum requirement of a passing test.

The corrosion properties of the Formulation I and II solutions were tested by immersing a carbon steel scalpel blade, a brass fitting, a "nickel silver" skin closure clip and a pair of chrome-plated scissors in the respective solution in a glass container at a temperature of 40° C. The results are shown in Table 1C. ("Nickel silver" is an alloy of copper, nickel and zinc.)

TABLE 1C

Corrosion/Stability Studies on Hydrogen Peroxide Sterilizing/Disinfecting Solutions at 40° C.

| Observations | Formulation I After 6 days | Formulation II After 6 days | Comm. Available Hydrogen Peroxide Solution-After 3 Hours |
|---|---|---|---|
| hydrogen peroxide | 6.30% | 6.02% | — |
| pH | 5.4 | 5.3 | ca. 1.8 |
| precipitate | none | none | heavy ppt. |
| carbon steel | untarnished | untarnished | untarnished |
| brass | untarnished | untarnished | tarnished |
| nickel silver | untarnished | untarnished | tarnished |
| chrome | untarnished | untarnished | — |

The presence of a precipitate in the solution indicates that the metal has been removed from the samples and precipitated from the solution.

EXAMPLE 2

A formulation of the present invention containing:
6% hydrogen peroxide
0.2% HEEDTA
0.15% sodium n-decyl diphenylether disulfonate (DOWFAX 3B2, Dow Chemical Co.)
0.3% sodium cocoyl sarcosinate
0.1% ZnSO$_4$.7H$_2$O
water to 100%

The formulation also contains sufficient acetic acid to give a resultant pH of 5.0 and 0.1% of a nonionic surfactant which consists of condensates of ethylene oxide with propylene glycol and propylene oxide (PLURONIC P104).

The formulation was tested against various organisms at 20° C. In some tests the formulation was diluted with water in a ratio of 1 part formulation to 2 parts water to determine the effect of the dilution on the activity. The results are presented in Table 2. The results shown that at a peroxide concentration of 3% (1:2 dilution), the formulation is not effective against certain organisms, i.e., S. aureus and M. tuberculosis.

TABLE 2

| Microorganisms | Exposure Time (Min.) | Dilution | Failure Rate |
|---|---|---|---|
| S. aureus[a] | 10 | undiluted | 5/30 |
| | 20 | undiluted | 0/60 |
| | 20 | 1:2 | 44/60 |
| P. aeruginosa[a] | 20 | undiluted | 1/60 |
| | 20 | 1:2 | 1/60 |
| S. choleraesuis[a] | 20 | undiluted | 0/60 |
| | 20 | 1:2 | 0/60 |
| T. mentagrophytes[b] | 5 | undiluted | passed |
| | 10 | undiluted | passed |
| | 15 | undiluted | passed |
| | 5 | 1:2 | passed |
| | 10 | 1:2 | passed |
| | 15 | 1:2 | passed |
| M. tuberculosis[c] | 20 | undiluted | 0/80 |
| | 20 | 1:2 | 30/80 |

The Environmental Protection Agency considered a failure rate of 1/60 as a "pass" for A.O.A.C. Use Dilution Test.
[a]A.O.A.C. Use Dilution Test
[b]A O.A.C. Fungicidal Test
[c]A.O.A.C. Tuberculocidal Test

EXAMPLE 3

This Example shows that the amount of hydrogen peroxide in the formulation may be reduced to 4% without any reduction in sporicidal activity. Formulations were prepared at 5% and 4% hydrogen peroxide concentrations. In addition to the hydrogen peroxide, the formulations contained:

0.3% HEEDTA
0.1% $ZnSO_4 \cdot 7H_2O$
0.3% Sodium cocoyl sarcosinate
0.15% Sodium n-decyl diphenylether disulfonate (DOWFAX 3B2)
95% Water The solution were adjusted to pH 5 with acetic acid or sodium hydroxide.

The solutions were tested against various spores at 40° C. with exposure times of 45 minutes. The results of the tests are given in Table 3.

TABLE 3

| Spores | % $H_2O_2$ | Carriers | Failure Rates |
|---|---|---|---|
| B. subtilis | 5 | Suture | 0/30 |
| | | Porcelain | 0/30 |
| | 4 | Suture | 0/30 |
| | | Porcelain | 0/30 |
| C. sporogenes | 5 | Suture | 0/30 |
| | | Porcelain | 0/30 |
| | 4 | Suture | 0/30 |
| | | Porcelain | 0/30 |

EXAMPLE 4

In order to show the necessity of various ingredients in the present solution, a series of 29 formulations were prepared with some ingredients omitted or the concentrations changed. All of the formulations contained 6% hydrogen peroxide. The composition of the formulations is shown in Table 4A. The corrosiveness of the formulations was then determined by immersing metal specimens in the solutions at 40° C. for six days. The metal specimens included a carbon steel scalpel blade, "nickel silver" skin closure clip and a copper fitting. A solution is not acceptable if the solution transparency is poor; if there is a heavy precipitate; if the dissolved metal is greater than 100 ppm; or, if the metal specimens are indicated to be poor. The solutions in which the final pH was above 6 is a result of a high initial pH or a high level corrosion of the metal and the loss of hydrogen peroxide. The results of the testing is shown in Table 4B.

An examination of the results set forth in Tables 4A and 4B indicates that hydrogen peroxide solutions must contain the surfactants and chelating agent specified herein and be maintained at the proper pH in order to obtain the desired non-corrosive properties.

TABLE 4A

| No. | $ZnSO_4 7H_2O$ (%) | Surfactants (% active) A | B | C | Chelating Agent Type | % | Initial pH | Final pH |
|---|---|---|---|---|---|---|---|---|
| 1 | .1 | .3 | .15 | .1 | HEEDTA | .3 | 5.0 | 5.0 |
| 2 | .1 | .3 | — | .1 | HEEDTA | .3 | 5.0 | 5.2 |
| 3 | .1 | — | .15 | .1 | HEEDTA | .3 | 5.0 | 8.0 |
| 4 | .1 | — | — | .1 | HEEDTA | .3 | 5.0 | 8.7 |
| 5 | — | .3 | .15 | .1 | HEEDTA | .3 | 5.0 | 4.6 |
| 6 | — | .3 | .15 | .1 | — | — | 5.0 | 4.1 |
| 7 | .1 | .3 | .15 | .1 | HEEDTA | .1 | 5.0 | 5.1 |
| 8 | .1 | .3 | .15 | .1 | HEEDTA | .2 | 5.0 | 4.9 |
| 9 | .1 | .3 | .15 | .1 | HEEDTA | .4 | 5.0 | 4.9 |
| 10 | .1 | .1 | .15 | .1 | HEEDTA | .3 | 5.0 | 4.9 |
| 11 | .1 | .4 | .15 | .1 | HEEDTA | .3 | 5.0 | 5.0 |
| 12 | .1 | .3 | .15 | .1 | HEEDTA | .3 | 3.3 | 5.0 |
| 13 | .1 | .3 | .15 | .1 | HEEDTA | .3 | 4.0 | 4.2 |
| 14 | .1 | .3 | .15 | .1 | HEEDTA | .3 | 6.0 | 8.2 |
| 15 | .1 | .3 | .15 | .1 | HEEDTA | .3 | 7.0 | 8.1 |
| 16 | .1 | .3 | .15 | — | HEEDTA | .3 | 5.0 | 5.0 |
| 17 | .1 | .3 | .15 | .1 | EDTA | .1 | 5.0 | 5.0 |
| 18 | .1 | .3 | .15 | .1 | EDTA | .2 | 5.0 | 5.2 |
| 19 | .1 | .3 | .15 | .1 | EDTA | .3 | 5.0 | 5.0 |
| 20 | .1 | .3 | .15 | .1 | EDTA | .4 | 5.0 | 4.7 |
| 21 | .1 | .3 | .15 | .1 | DTPA | .1 | 5.0 | 4.4 |
| 22 | .1 | .3 | .15 | .1 | DTPA | .2 | 5.0 | 4.9 |
| 23 | .1 | .3 | .15 | .1 | DTPA | .3 | 5.0 | 5.2 |
| 24 | .1 | .3 | .15 | .1 | DPA | .4 | 5.0 | 7.6 |
| 25 | .1 | .3 | .15 | .1 | DPA | .5 | 5.0 | 7.3 |
| 26 | .1 | .3 | .15 | .1 | DTPA | .3 | 4.0 | 4.9 |
| 27 | .1 | .3 | .15 | .1 | DTPA | .3 | 4.5 | 4.8 |
| 28 | .1 | .3 | .15 | .1 | DTPA | .3 | 5.5 | 4.8 |
| 29 | .1 | .3 | .15 | .1 | DTPA | .3 | 6.0 | 4.8 |

A - Sodium cocyl sarcosinate
B - Sodium n-decyl diphenylether disulfonate
C - Nonionic surfactant - condensate of ethylene oxide with propylene glycol and propylene oxide.

TABLE 4B

| No. | Loss of $H_2O_2$ % | Solution Transparency | Color | Precipitate | Dissolved Metals (ppm) Fe | Cu | Metal Specimens |
|---|---|---|---|---|---|---|---|
| 1 | 9 | fair | sl. blue | none | .45 | 65.1 | good |
| 2 | 7 | poor | sl. blue | none | .40 | 65.1 | good |
| 3 | 100 | fair | sl. green | heavy | .10 | 103 | poor |
| 4 | 100 | fair | sl. yellow | heavy | .15 | 48.3 | poor |
| 5 | 18 | poor | colorless | none | .50 | 77.7 | good |
| 6 | 26 | poor | colorless | none | .30 | 54.6 | good |
| 7 | 8 | good | colorless | none | .30 | 23.1 | good |
| 8 | 0 | fair | sl. blue | none | .40 | 54.6 | good |
| 9 | 5 | fair | sl. blue | none | .50 | 103 | good |
| 10 | 4 | excellent | sl. blue | none | .40 | 50.4 | good |
| 11 | 12 | poor | sl. blue | none | .50 | 77.7 | good |
| 12 | 8 | good | blue | none | .20 | 2,778 | poor |
| 13 | 6 | poor | sl. blue | none | .60 | 176 | good |
| 14 | 9 | good | sl. green | heavy | .15 | 109 | poor |

TABLE 4B-continued

| No. | Loss of H₂O₂ % | Solution Trans-parency | Solution Color | Precip-itate | Dissolved Metals (ppm) Fe | Dissolved Metals (ppm) Cu | Metal Speci-mens |
|---|---|---|---|---|---|---|---|
| 15 | 4 | fair | sl. green | heavy | .10 | 134 | poor |
| 16 | 7 | fair | sl. blue | none | .4 | 65.1 | good |
| 17 | 0 | good | colorless | none | .25 | 19 | good |
| 18 | 0 | good | sl. blue | none | .20 | 81 | good |
| 19 | 2 | fair | sl. blue | none | .20 | 109 | fair |
| 20 | 4 | fair | sl. blue | none | .25 | 55 | good |
| 21 | 0 | good | sl. blue | none | .25 | 63 | fair |
| 22 | 0 | good | colorless | none | .25 | 40 | good |
| 23 | 0 | excellent | colorless | none | .20 | 25 | good |
| 24 | 100 | poor | blue | heavy | .10 | 380 | poor |
| 25 | 100 | poor | blue | heavy | .15 | 410 | poor |
| 26 | 0 | good | colorless | none | .25 | 36 | good |
| 27 | 3 | good | colorless | none | .25 | 44 | good |
| 28 | 0 | good | colorless | none | .25 | 40 | good |
| 29 | 0 | good | colorless | none | .25 | 42 | good |

It is claimed:

1. An aqueous disinfecting solution having a buffered pH of from 4 to 6.0 and which is not corrosive to surgical instruments comprising from 4% to 6% by weight hydrogen peroxide, from 0.1% to 0.3% by weight of an anionic surfactant selected from the group consisting of sodium lauryl sulfate and sodium n-decyl diphenylether disulfonate; from 0.1% to 0.3% by weight of a sarcosinate surfactant selected from the group consisting of sodium cocoyl sarcosinate and sodium lauryl sarcosinate; 0.1% by weight of a soluble zinc compound selected from the group consisting of zinc sulfate, zinc acetate, zinc nitrate and zinc gluconate and from 0.1% to 0.3% by weight of a nitrogen containing chelating agent selected from the group consisting of N-(hydroxyethyl) ethylenediamine triacetic acid, ethylenediamine tetraacetic acid and diethylenetriamine pentaacetic acid.

2. An aqueous disinfecting solution of claim 1 in which the anionic surfactant is sodium n-decyl diphenyl ether disulfonate; the sarcosinate surfactant is sodium cocoyl sarcosinate; and, the soluble zinc compound is zinc sulfate, and the chelating agent is N-(hydroxylethyl) ethylenediamine triacetic acid.

3. A process of disinfecting metallic surgical instruments without excessively corroding the instruments comprising contacting said instruments with a solution having a buffered pH of from 4 to 6.0 and comprising from 4% to 6% by weight hydrogen peroxide, from 0.1% to 0.3% by weight of an anionic surfactant selected from the group consisting of sodium lauryl sulfate and sodium n-decyl diphenylether disulfonate; from 0.1% to 0.3% by weight of a sarcosinate surfactant selected from the group consisting of sodium cocoyl sarcosinate and sodium lauryl sarcosinate; 0.1% by weight of a soluble zinc compound selected from the group consisting of zinc sulfate, zinc acetate, zinc nitrate and zinc gluconate and from 0.1% to 0.3% by weight of a nitrogen containing chelating agent selected from the group consisting of N-(hydroxy-ethyl) ethylenediamine triacetic acid, ethylenediamine tetraacetic acid and diethylenetriamine pentaacetic acid.

4. The process of claim 3 in which the anionic surfactant is sodium n-decyl diphenylether disulfonate; the sarcosinate surfactant is sodium cocoyl sarcosinate; and, the soluble zinc compound is zinc sulfate, and the chelating agent is N-(hydroxylethyl) ethylenediamine triacetic acid.

* * * * *